United States Patent
Leu et al.

(10) Patent No.: US 7,528,373 B2
(45) Date of Patent: May 5, 2009

(54) METHOD AND SYSTEM FOR DETECTION OF GAS LEAKAGE SOURCES

(75) Inventors: Gen-Hou Leu, Taipei (TW); Shaw-Yi Yan, Hsinchu County (JP); Hui-Ya Shih, Changhua (TW); Sheng-Jen Yu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/481,450

(22) Filed: Jul. 6, 2006

(65) Prior Publication Data

US 2007/0007450 A1 Jan. 11, 2007

(30) Foreign Application Priority Data

Jul. 6, 2005 (TW) .............................. 94122838 A

(51) Int. Cl.
*G01J 5/02* (2006.01)
(52) U.S. Cl. .............................. 250/339.08; 250/338.5; 250/339.12; 250/343; 702/24; 702/28
(58) Field of Classification Search ............ 250/339.02, 250/339.08, 338.5, 339.12, 343; 702/24, 702/28
See application file for complete search history.

(56) References Cited

U.S. PATENT DOCUMENTS

| | | | | |
|---|---|---|---|---|
| 4,795,253 A | * | 1/1989 | Sandridge et al. ............ 356/51 |
| 5,430,293 A | * | 7/1995 | Sato et al. .................... 250/330 |
| 6,542,242 B1 | * | 4/2003 | Yost et al. .................... 356/450 |
| 6,862,535 B2 | * | 3/2005 | Binder ........................ 702/24 |
| 6,900,439 B2 | * | 5/2005 | Komiyama et al. .... 250/339.08 |
| 7,194,369 B2 | * | 3/2007 | Lundstedt et al. ........... 702/104 |
| 2004/0124357 A1 | * | 7/2004 | Leu et al. ............... 250/339.08 |
| 2004/0157347 A1 | * | 8/2004 | Komiyama et al. ............. 438/8 |
| 2005/0159899 A1 | * | 7/2005 | Komiyama et al. ........... 702/24 |
| 2007/0045542 A1 | * | 3/2007 | Hashmonay ........... 250/339.12 |

* cited by examiner

*Primary Examiner*—David P Porta
*Assistant Examiner*—David S Baker
(74) *Attorney, Agent, or Firm*—Quintero Law Office

(57) ABSTRACT

A system for detection of gas leakage sources. An open-path FTIR detection system is located before the return filter of recirculating air of a factory to detect gas composition of recirculating air and transmits the result to a data server through a communication network. A multi-port extractive FTIR system is located in the factory to collect and detect gas sample of local area air using pipelines located in different areas and transmits the result of gas composition to the data server through the communication network. An IR monitor system obtains the gas composition from the data server through the communication network. A process exhaust management system obtains the gas composition from the IR monitor system through the communication network for the analysis of a gas leakage source.

10 Claims, 3 Drawing Sheets

METHOD AND SYSTEM FOR DETECTION OF GAS LEAKAGE SOURCES

BACKGROUND OF THE INVENTION

1. Field of the Invention

The invention relates to a detection system and method, and in particular to a system and method for detection of gas leakage sources for semiconductor processes.

2. Description of the Related Art

Multiple kinds of chemical materials have been used in LCD (Liquid Crystal Display) and semiconductor industries and some are dangerous, such that gas leakage may occur due to accidents, thereby damaging manufacturing and production workers. To prevent such damage due to gas leakage, a large number of gas detectors are used in LCD and semiconductor manufactories. Currently, gas detector comprises catalytic combustible gas detectors, solid-state gas detectors, electrochemical gas detectors, and the like.

A large number of gas detectors can monitor the occurrence of gas leakage but false alarms may occur. Gas detectors will alarm in some conditions that gas leakage does not occur, and it causes unnecessary cost loss. Correctly detecting leakage of process gas/exhaust and managing leakage sources to reduce unnecessary loss are thus important.

Thus, a system for detection of gas leakage sources for semiconductor processes is desirable.

BRIEF SUMMARY OF THE INVENTION

A system for detection of gas leakage sources applied to process control of a factory is provided, comprising a data server, an open-path FTIR gas detection system, a multi-port extractive FTIR gas detection system, an software module named "IR monitor system", and a software module named "process exhaust management system". The open-path FTIR gas detection system, located before the return filter of recirculating air of the factory, detects gas composition of recirculating air and transmits the result to the data server through a communication network. The multi-port extractive FTIR system, located in the factory, collects and detects gas sample of local area air using pipelines located in different areas and transmits the result of gas composition to the data server through the communication network. The IR monitor system obtains the gas composition from the data server through the communication network. The process exhaust management system obtains the gas composition from the IR monitor system through the communication network for the analysis of the gas leakage source.

A method for detection of gas leakage sources applied to process control of a factory comprises providing a data server, an open-path FTIR gas detection system, a multi-port extractive FTIR gas detection system, an IR monitor system, and a process exhaust management system, wherein the open-path FTIR detection system is located before the return filter of recirculating air in the factory, detecting recalculating gas using the open-path FTIR detection system and transmitting the result of gas composition to the data server through a communication network, collecting and detecting gas sample of local area air using the multi-port extractive FTIR gas detection system located in the factory via pipelines located in different areas and transmitting the result of gas composition to the data server through the communication network, obtaining the gas composition from the data server using the IR monitor system through the communication network, and obtaining the gas composition from the IR monitor system using the process exhaust management system through the communication network for the analysis of gas leakage source.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
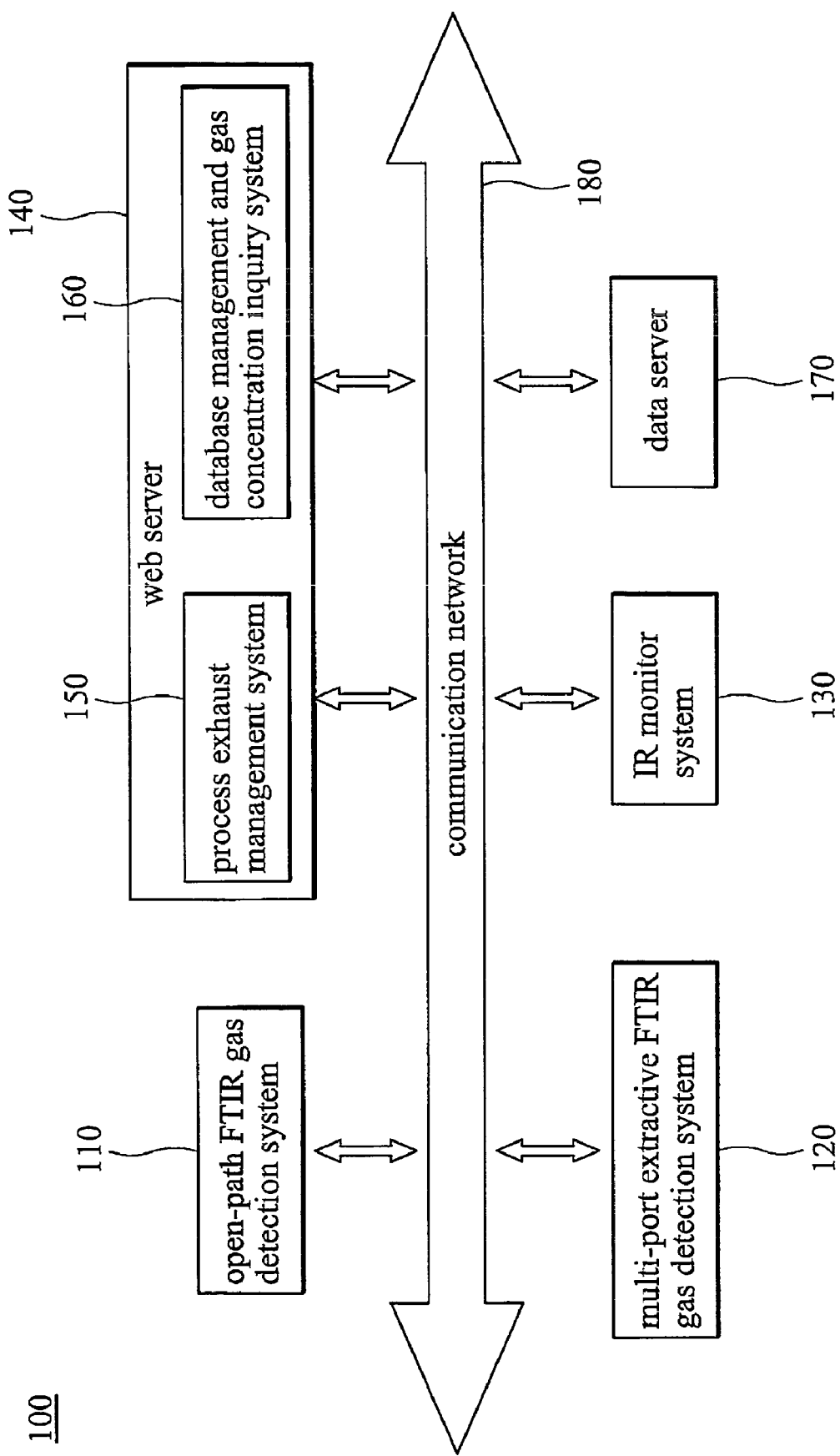
FIG. 1 is a schematic view of an embodiment of the architecture of a system for detection of gas leakage sources.

Several exemplary embodiments of the invention are described with reference to FIGS. 1 through 3, which generally relate to detection of gas leakage sources for semiconductor processes. It is to be understood that the following disclosure provides many different embodiments as examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The invention discloses a system and method for detection of gas leakage sources for semiconductor processes. An electronic process exhaust management system developed for this leak detection method of the invention integrates a Fourier transform infrared spectrometer (FTIR) and an air quality monitoring and alarm system to rapidly detect gas leakage sources and make factory can quickly recover from abnormal conditions.

FIG. 1 is a schematic view of an embodiment of the architecture of a system for detection of gas leakage sources.

Optical gas leakage source detection system 100 comprises an open-path FTIR gas detection system 110, a multi-port extractive FTIR gas detection system 120, an IR monitor system 130, a web server 140, and a data server 170. Web server 140 further comprises a process exhaust management system 150 and a database management and gas concentration inquiry system 160.

Gas leakage detection first detects abnormal states in the air. To detect various species of unreacted process gases and reacted process by-products, a sensitive and multi-species gas analyzer is required. Thus, open-path FTIR gas detection system 110 of the invention uses an open-path FTIR to detect gas in a clean room. Features of the open-path FTIR comprise a low detection limit, high sensitivity, and the ability to simultaneously detect more than 90% of process and byproduct gases. Open-path FTIR detection system 110 is located before a return filter of recirculating air of a factory to detect the air quality.

Additionally, multi-port extractive FTIR system 120 is collocated to detect gases at predetermined times and locations. The FTIR can reach the high sensitivity using liquid nitrogen and cooling mercury cadmium telluride (MCT) with 77K operating temperature. Multi-port extractive FTIR system 120 collects and detects gas using pipelines located in different areas and analyzes the collected gas using an extractive FTIR multi-gas analyzer.

Open-path FTIR gas detection system 110 and multi-port extractive FTIR gas detection system 120 transmit gas composition to data server 170 through a communication network (the Internet or Intranet) 180 for inquiry operations. IR monitor system 130 obtains latest information of multiple gas concentrations from data server 170 and executes a real-time update whenever data server 170 obtains updated result from gas monitoring system. Process exhaust management system 150 can search process information relating to abnormal gas leakage events. IR monitor system 130 alarms and automatically or manually activates process exhaust management system 150 when the detected gas concentration exceeds a threshold value. Process exhaust management system 150 is activated and retrieves information of hazardous leak gases from IR monitor system 130 for automatic analysis and displays analysis results to rapidly locate leaked pipelines or dry pumps. The result of analysis comprises time and locations of alarms, locations and process schedules of tools possibly responsible for the leak event.

Users can login to database management and gas concentration inquiry system 160 of web server 140 via communication network 180 to make direct gas detection information inquiries.

Figure 2:
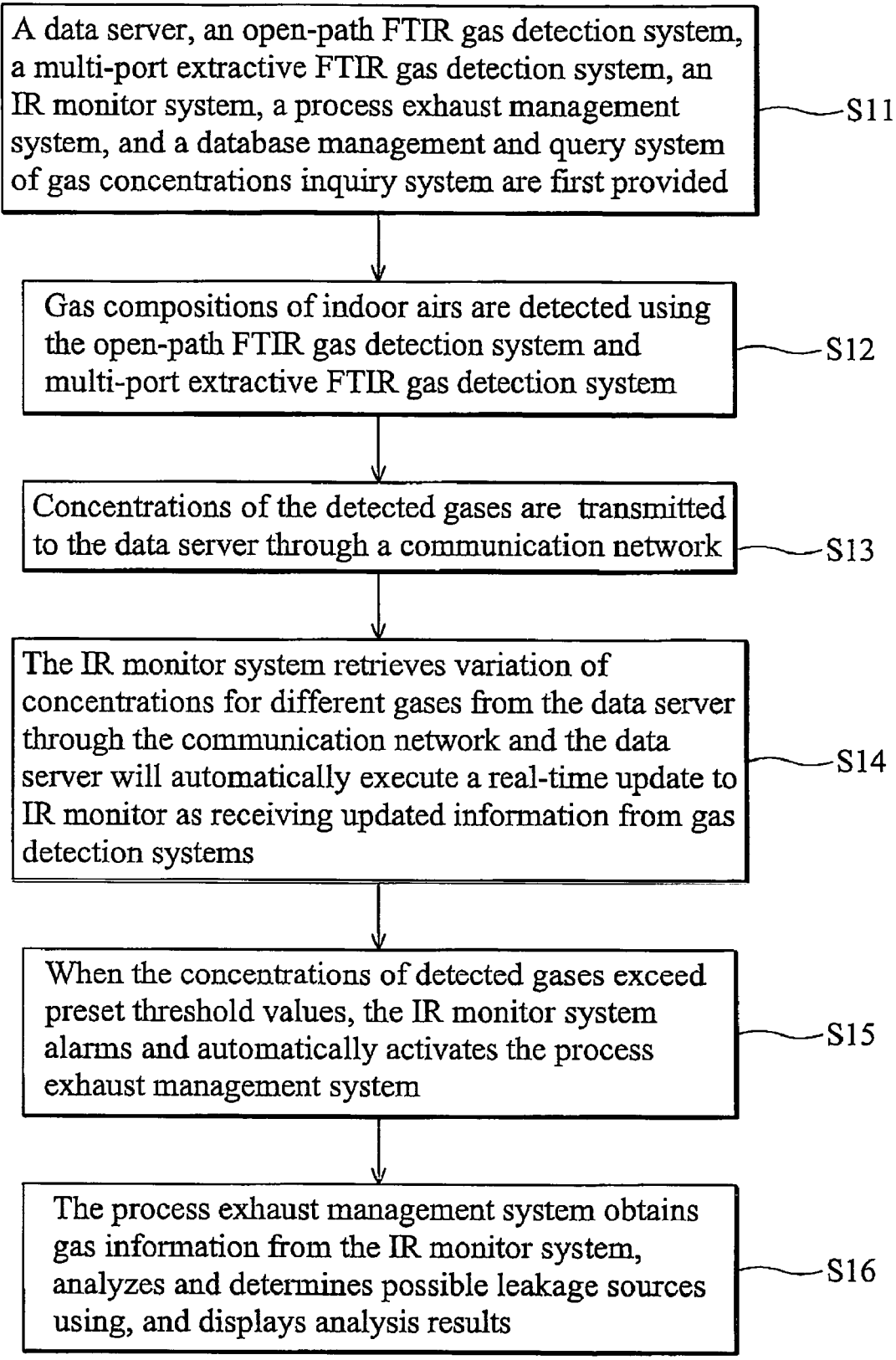
FIG. 2 is a flowchart of an embodiment of a method for detection of gas leakage sources.

FIG. 2 is a flowchart of an embodiment of a method for detection of gas leakage sources.

A data server, an open-path FTIR gas detection system, a multi-port extractive FTIR gas detection system, an IR monitor system, a process exhaust management system, and a database management and gas concentration inquiry system are first provided (step S11). Gas compositions of indoor airs are detected using the open-path FTIR gas detection system and multi-port extractive FTIR gas detection system (step S12), and concentrations of the detected gases are transmitted to the data server through a communication network (step S13). Next, the IR monitor system retrieves variation of concentrations for different gases from the data server through the communication network. The data server will automatically execute a real-time update to IR monitor as receiving updated information from gas detection systems (step S14). When the concentrations of detected gases exceed preset threshold values, the IR monitor system alarms and automatically activates the process exhaust management system for leaking search (step S15). The process exhaust management system obtains alarmed information consisting concentrations of hazardous gases from the IR monitor system, analyzes and determines possible leakage sources using build-in process information, and displays analysis results (step S16).

Another embodiment of the process exhaust management system is further described in the following.

Figure 3:
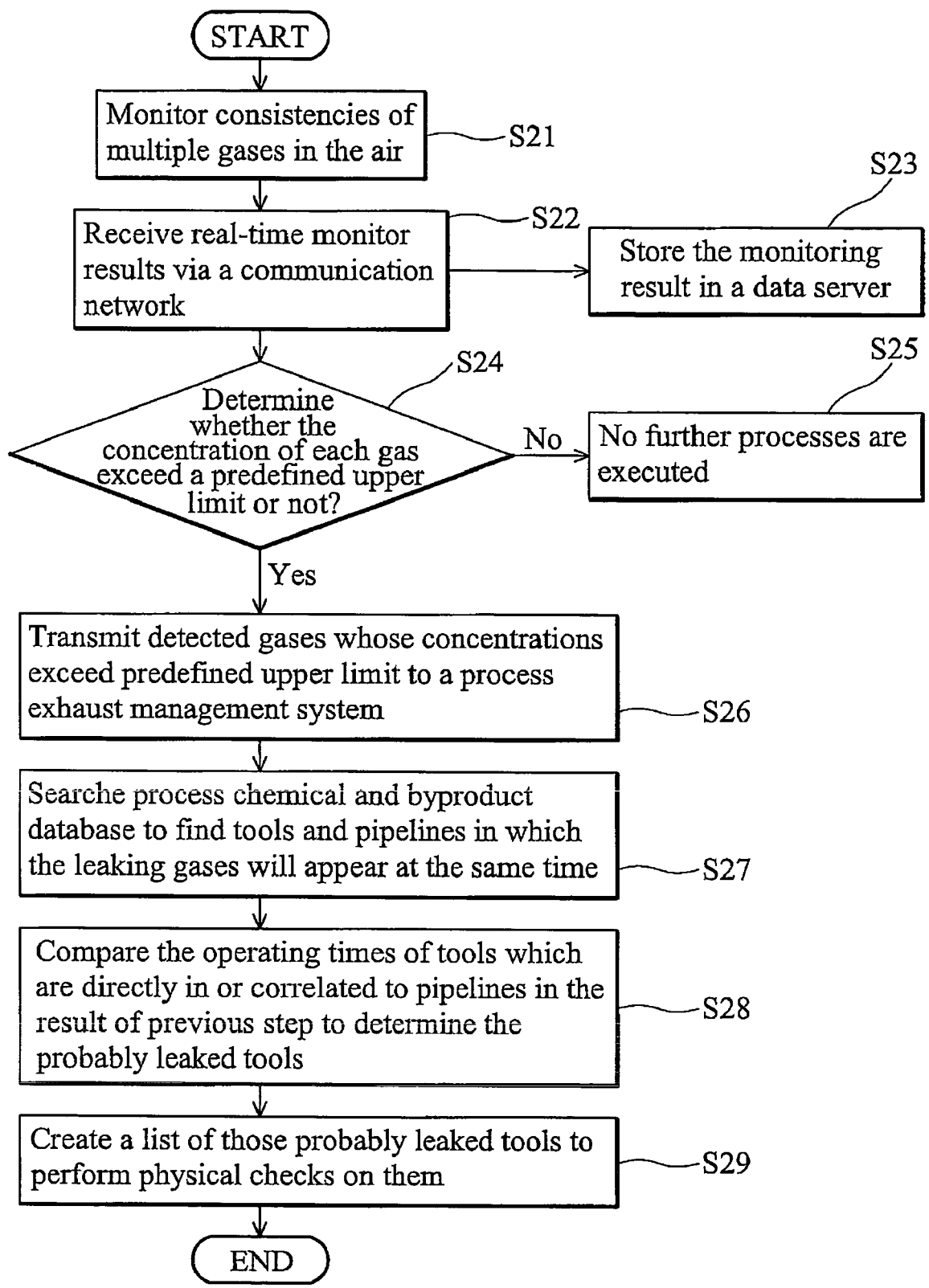
FIG. 3 is a flowchart of another embodiment of a method for detection of gas leakage sources.

FIG. 3 is a flowchart of another embodiment of a method for detection of gas leakage sources.

An open-path FTIR gas detection system and a multi-port extractive FTIR gas detection system monitors concentration of multiple gases in the air (step S21). Next, an IR monitor system receives real-time monitoring results via a communication network (step S22) and stores the results in a data server (step S23). It determines whether the concentration of each gas exceed a predefined upper limit or not (step S24). If not, no further processes are executed (step S25), and, if so, detected gases whose concentrations exceed the predefined upper limits are transmitted to a process exhaust management system (step S26).

Next, the process exhaust management system searches process chemical and byproduct database of tools and pipelines (not shown) to find tools and pipelines in which the leaking gases will appear at the same time (step S27). The step is equivalent to process exhaust management system 150 searching process information relating to abnormal gas leakage events. Located tools and pipelines are checked according to operating time stored in a tool operating time database (not shown) to determine probably leaked tools (step S28). A list recording probably leaked tools is generated to allow users performing physical checks on those candidates of leaking source (step S29).

Additionally, an IR monitor system is a common monitor application, acting like Advantech Studio software developed by the Advantech Corporation and Wonderware software developed by the Invensys Corporation, which are not detailed described in the embodiment.

A system for detection of gas leakage sources of the invention can be applied to detection of leakage of process chemicals, rapidly focusing on possible leakage sources to recover from abnormal conditions and reduce the personnel and property lose due to accidents.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A system for detection of gas leakage sources, applied to process control of a factory, comprising:
    a data server;
    an open-path FTIR detection system, located before the return filter of recirculating air of the factory, detecting leakage gas and transmitting gas composition to the data server through a communication network;
    a multi-port extractive FTIR system, located in the factory, collecting leakage gas using pipelines located in different areas and transmitting gas composition to the data server through the communication network;
    an IR monitor system, obtaining the gas composition from the data server through the communication network; and
    a process exhaust management system, obtaining the gas composition from the IR monitor system through the communication network for the analysis of possible gas leakage source and determining a gas leakage source according to analysis results and the gas composition.

2. The system for detection of gas leakage sources as claimed in claim 1, further comprising a database management and gas concentration inquiry system, inquiring about the gas composition stored in the data server.

3. The system for detection of gas leakage sources as claimed in claim 1, wherein, when the detected gas concentrations exceeds a threshold value, the IR monitor system alarms and automatically activates the process exhaust management system.

4. The system for detection of gas leakage sources as claimed in claim 1, wherein the IR monitor system executes a real-time update whenever the data server obtains gas composition of detected gas.

5. The system for detection of gas leakage sources as claimed in claim 1, wherein the multi-port extractive FTIR system obtains and analyzes gas composition of an area where the pipelines are located.

6. A method for detection of gas leakage sources, applied to process control of a factory, comprising:

providing a data server, an open-path FTIR detection system, a multi-port extractive FTIR system, an IR monitor system, and a process exhaust management system, wherein the open-path FTIR detection system is located before the return filter of recirculating air of the factory;

detecting leakage gas using the open-path FTIR detection system and transmitting gas composition of the detected gas to the data server through a communication network;

collecting gas using the multi-port extractive FTIR system located in the factory via pipelines located in different areas and transmitting gas composition to the data server through the communication network;

obtaining the gas composition from the data server using the IR monitor system through the communication network; and obtaining the gas composition from the IR monitor system using the process exhaust management system through the communication network for the analysis of possible gas leakage sources and determining a gas leakage source according to analysis to results and the gas composition.

7. The method for detection of gas leakage sources as claimed in claim 6, further comprising inquiring the gas composition stored in the data server using a database management and gas concentration inquiry system.

8. The method for detection of gas leakage sources as claimed in claim 6, further comprising the IR monitor system alarming and automatically activating the process exhaust management system when the detected gas concentration exceeds a threshold value.

9. The method for detection of gas leakage sources as claimed in claim 6, further comprising the IR monitor system executing a real-time update whenever the data server receives gas composition of detected leakage gas.

10. The method for detection of gas leakage sources as claimed in claim 6, further comprising the multi-port extractive FTIR system obtaining and analyzing gas composition of an area where the pipelines are located.

* * * * *

UNITED STATES PATENT AND TRADEMARK OFFICE
CERTIFICATE OF CORRECTION

PATENT NO.       : 7,528,373 B2             Page 1 of 1
APPLICATION NO.  : 11/481450
DATED            : May 5, 2009
INVENTOR(S)      : Gen-Hou Leu et al.

It is certified that error appears in the above-identified patent and that said Letters Patent is hereby corrected as shown below:

Title Pg, Item (75), Inventors:

"Shaw-Yi Yan, Hsinchu County (JP)" should be -- Shaw-Yi Yan, Hsinchu County (TW) --

Signed and Sealed this

Ninth Day of June, 2009

JOHN DOLL
*Acting Director of the United States Patent and Trademark Office*